(12) United States Patent
Prance et al.

(10) Patent No.: US 8,264,247 B2
(45) Date of Patent: Sep. 11, 2012

(54) ELECTRIC POTENTIAL SENSOR

(75) Inventors: Robert Prance, Brighton (GB);
Christopher Harland, Brighton (GB)

(73) Assignee: University of Sussex (GB)

(*) Notice: Subject to any disclaimer, the term of this patent is extended or adjusted under 35 U.S.C. 154(b) by 364 days.

(21) Appl. No.: 12/293,872

(22) PCT Filed: Feb. 13, 2007

(86) PCT No.: PCT/GB2007/000490
§ 371 (c)(1),
(2), (4) Date: Mar. 3, 2009

(87) PCT Pub. No.: WO2007/107689
PCT Pub. Date: Sep. 27, 2007

(65) Prior Publication Data
US 2009/0309605 A1    Dec. 17, 2009

(30) Foreign Application Priority Data

Mar. 21, 2006 (GB) .................................. 0605717.8

(51) Int. Cl.
*G01R 27/26* (2006.01)
*G01R 19/00* (2006.01)
(52) U.S. Cl. .................. 324/713; 324/658; 324/686
(58) Field of Classification Search ........... 324/600–719
See application file for complete search history.

(56) References Cited

U.S. PATENT DOCUMENTS

| | | | |
|---|---|---|---|
| 3,404,341 A | 10/1968 | Young | |
| 3,611,127 A * | 10/1971 | Vosteen | 324/72 |
| 3,729,675 A | 4/1973 | Vosteen | |
| 3,880,146 A * | 4/1975 | Everett et al. | 600/523 |
| 5,663,680 A * | 9/1997 | Nordeng | 330/9 |
| 5,986,456 A * | 11/1999 | Yamashita | 324/457 |
| 6,316,942 B1 * | 11/2001 | Horiguchi | 324/457 |
| 6,686,800 B2 | 2/2004 | Krupka | |
| 6,961,601 B2 | 11/2005 | Matthews et al. | |
| 7,088,175 B2 | 8/2006 | Krupka | |
| 7,466,148 B2 * | 12/2008 | Fridman et al. | 324/686 |
| 7,518,443 B2 | 4/2009 | Matthews | |
| 2006/0058694 A1 * | 3/2006 | Clark et al. | 600/509 |

FOREIGN PATENT DOCUMENTS

| | | |
|---|---|---|
| EP | 1281976 A1 | 2/2003 |
| EP | 1364614 A1 | 11/2003 |
| GB | 2158592 A | 11/1985 |
| GB | 2250822 A | 6/1992 |

(Continued)

OTHER PUBLICATIONS

International Search Report for PCT/GB2007/000490, Jul. 27, 2007.

(Continued)

*Primary Examiner* — Melissa Koval
*Assistant Examiner* — Emily Chan
(74) *Attorney, Agent, or Firm* — Brooks Kushman P.C.

(57) ABSTRACT

The present invention provides an electric potential sensor for the measurement of potentials non-invasively. The sensor comprises at least one detection electrode arranged for capacitive coupling with a sample under test and for generating a measurement signal, and a sensor amplifier adapted to receive the measurement signal as input and to supply an amplified detection signal as output. Input impedance enhancing means are included for providing a high input impedance to the sensor amplifier for increasing the sensitivity of the electrode to reduced electric potentials, and a discrete pre-amplifier stage is arranged to co-operate with the sensor amplifier to reduce the input capacitance of the amplifier.

14 Claims, 5 Drawing Sheets

FOREIGN PATENT DOCUMENTS

| | | |
|---|---|---|
| WO | 01/31351 A1 | 5/2001 |
| WO | 2002019524 A1 | 3/2002 |
| WO | 03/048789 A2 | 6/2003 |

OTHER PUBLICATIONS

Lanyi, The Noise of Input Stages With Low Parasitic Capacitance, Sep. 2001, Measurement Science and Technology, vol. 12, No. 9, pp. 1456-1464.

Manetakis et al., Driven-Shield Amplifier for the Recording of Broadband, Nano-Amp Scale, Current Transients From Sources Located Inside a Vacuum Chamber, May 1, 1995, Measurement Science and Technology, vol. 6, No. 5, pp. 571-575.

Prance et al., An Ultra-Low-Noise Electrical-Potential Probe for Human-Body Scanning, Mar. 1, 2000, Measurement Science and Technology, vol. 11, No. 3, pp. 291-297.

\* cited by examiner

ELECTRIC POTENTIAL SENSOR

TECHNICAL FIELD

The present invention concerns electric potential sensors for use for the measurement of potentials non-invasively in a wide variety of applications, for example in the fields of medical diagnostics and biometric sensing.

BACKGROUND OF THE INVENTION

In order to create a sensitive electrodynamic measuring device, it is customary to provide a high input impedance and thereby reduce the power of the input signal required to operate the device. However, electronic circuits with a very high input impedance tend to be unstable, and so practical devices are usually a compromise between achieving the necessary degree of sensitivity, providing the desired input impedance and ensuring an acceptable degree of stability.

In International Patent Application No. WO 03/048789, an electrodynamic sensor is disclosed in which different circuit techniques are combined to achieve several orders of magnitude improvement in sensitivity, by comparison with previously known electrodynamic sensors, whilst still maintaining sufficient stability to permit a relatively unskilled operator to make measurements in everyday conditions. According to this earlier application, an electrodynamic sensor is provided, which comprises a high input impedance electrometer adapted to measure small electrical potentials originating from an object under test by means of at least one input probe, which has no direct electrical contact with the object. The circuit arrangement of the electrometer of this invention comprises an amplifier which includes a combination of ancillary circuits arranged cumulatively to increase the sensitivity of said electrometer to said small electrical potentials whilst not perturbing the electrical field associated therewith, the ancillary circuits serving to provide at least two of guarding, bootstrapping, neutralisation, supply rail drift correction, supply modulation and offset correction for said sensor.

Whilst these features assist in providing a sensor with high input impedance and a relatively stable operation, nevertheless, in situations where there may be weak capacitive coupling to, or a signal of small amplitude generated by, a source or sample under test, noise problems may still remain and may inhibit or prevent accurate signal measurement. This is particularly the case in certain medical and microscopic applications in which there is only a weak capacitive coupling and yet highly accurate signal measurement is essential, for example in a remote off-body mode of sensing in which the or each probe has no physical contact with the human body and typically the weak capacitive coupling would be <1 pF.

More particularly, in applications where there is a weak coupling between a sample under test and the sensor electrode, the capacitive coupling to the sample may be comparable with or much smaller than the input capacitance of the sensor. In this case, the measurement signal received by the sensor is attenuated by the capacitive potential divider formed by the coupling capacitance and the input capacitance and may be difficult to capture.

There is thus a significant need for an electric potential sensor in which the possibility for accurate signal measurement is enhanced in cases of weak capacitive coupling to a sample under test.

Such a need is especially pronounced in cases where accuracy of signal measurement is crucial, for example in cases of biometric and medical measurement.

There is also a significant need for an electric potential sensor in which the signal to noise ratio is substantially improved.

BRIEF SUMMARY OF THE INVENTION

The present invention seeks to overcome the problems described above and to provide a novel electric potential sensor which is capable of highly accurate and non-invasive signal measurement.

The present invention, at least in the preferred embodiments described below, also seeks to provide an electric potential sensor in which the signal to noise ratio is significantly enhanced.

The present invention further seeks to provide various techniques and combinations of techniques for enhancing the signal to noise ratio in an electric potential sensor.

According to the invention, there is provided an electric potential sensor comprising:
- at least one detection electrode arranged for capacitive coupling with a sample under test and for generating a measurement signal;
- a sensor amplifier adapted to receive the measurement signal as input and to supply an amplified detection signal as output;
- input impedance enhancing means for providing a high input impedance to the sensor amplifier for increasing the sensitivity of the electrode to reduced electric potentials; and
- a discrete pre-amplifier stage arranged to co-operate with the sensor amplifier to reduce the input capacitance of the amplifier.

According to the invention, the discrete pre-amplifier stage serves to increase the amplitude of the input measurement signal and thereby to increase the signal to noise ratio and enhance signal measurement. The discrete pre-amplifier stage may, for example, be provided by a high electron mobility transistor, or a FET arrangement.

The input impedance enhancing means may comprise at least one of a guard circuit, a bootstrapping circuit and a neutralisation circuit. The input impedance enhancing means may also further comprise one or more circuits for supply rail drift correction, supply modulation and offset correction for the sensor.

In a preferred embodiment described below, the detection electrode is juxtaposed with a conducting element connected to a zero reference potential in order to reduce effective source impedance, the conducting element being in the form of an annular ring surrounding the detection electrode.

In a further embodiment of the invention, there is provided in addition means for reducing the noise amplitude in order to increase the signal to noise ratio. For example, such means for reducing the noise amplitude may comprise at least one of a dc stability gain setting circuit, a noise matching circuit, and an enhanced bootstrap circuit.

The present invention thus aims to increase the signal to noise ratio either by increasing the amplitude of the signal or by decreasing the amplitude of the noise or both.

BRIEF DESCRIPTION OF THE DRAWINGS

The present invention will now be described further, by way of example, with reference to the accompanying drawings, in which.

DETAILED DESCRIPTION OF INVENTION

Figure 1:
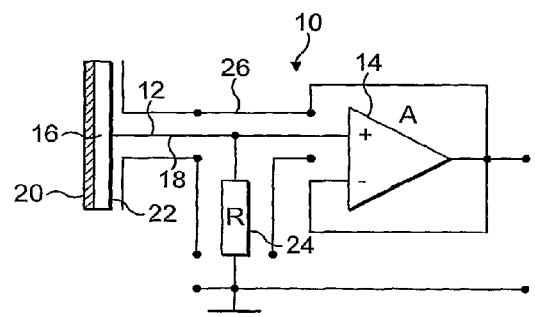
FIG. 1 is a circuit diagram of an electrodynamic sensor according to the prior art.

Referring to FIG. 1, an electrodynamic sensor as disclosed in International Patent Application No. WO 03/048789 will first be described.

As shown in FIG. 1, an eletrodynamic sensor 10 according International Patent Application number WO 03/048789 comprises a detection electrode 12 connected to the non-inverting input of a sensor amplifier 14. In use, the detection electrode 12 supplies a measurement signal to the sensor amplifier 14, whose output supplies an amplified detection signal as output.

The detection electrode 12 includes an electrode disc 16 mounted on a conductive stem 18, the electrode disc 16 comprising a surface oxide layer 20 on a substrate 22. The sensor amplifier 14 has a fixed input resistance 24, connected between the electrode 12 and the non-inverting input of the amplifier 14, to provide a steady input bias current to the amplifier 14. In practice, the input resistor 24 will generally have a high resistance of the order of 100 GΩs or greater. The sensor amplifier 14 also has a guard 26 physically surrounding the input circuitry including the electrode 12 and the resistor 24 and providing a shield driven by the output of the amplifier 14. Stray capacitance is thus alleviated by means of this positive feedback technique by maintaining the same potential on the guard or shield 26 as on the input detection electrode 12.

In addition to the guard 26, further circuit components may be provided for bootstrapping and neutralisation of the sensor as described in International Patent Application number WO 03/048789.

The earlier sensor shown in FIG. 1 may be employed as a sensor probe for electrodynamic body sensing to obtain biometric measurements either in a contact mode, in which case the oxide layer 20 forms a capacitor providing relatively strong electrical coupling to the skin of a person under observation, or in an electrically isolated sensing mode, in which case the oxide layer 20 may be omitted and capacitive couple providing a relatively weak electrical coupling may be achieved through clothing or other intervening layers.

A sensor 28 according to the present invention will now be described with reference to FIG. 2, such sensor effectively comprising the sensor 10 of FIG. 1, with its detection electrode 12 and sensor amplifier 14, but with the inclusion of further and different components to increase the accuracy of signal measurement, particularly in cases where a weak capacitive coupling to the subject under test is present.

One such additional component comprises an annular conducting element 12a surrounding the electrode 12 and connected to a reference voltage potential $V_r$, such as earth or a zero potential point on the sensor amplifier 14. The effect of the annular element 12a is to reduce the source impedance, ie the coupling impedance between the sample under test and the input of the sensor amplifier 14 as provided by a combination of coupling resistance $R_c$ and coupling capacitance $C_c$, by reducing the effective distance from the electrode 12 to the earthing point for the sensor amplifier 14. The element 12a does not need to be annular but may have other configurations.

Further additional components are included in the circuitry of the sensor itself. More particularly, the sensor 28 of the present invention employs a discrete pre-amplifier stage 30, having an intrinsically lower device input capacitance than is available in commercial operational amplifiers, in conjunction with the features of the sensor 10 of FIG. 1. Such a discrete pre-amplifier stage 30 is shown diagrammatically in FIG. 2, and embodiments of this discrete device are described with reference to FIGS. 3 to 6. The invention may also employ various bootstrapping techniques in conjunction with the pre-amplifier stage 30 in order to enhance the operation of the discrete device, as shown for example respectively in FIGS. 2 to 6. In addition, or instead, the invention may employ techniques for reducing the amplitude of the noise, as shown for example in FIGS. 2 and 7 to 9.

Figure 2:
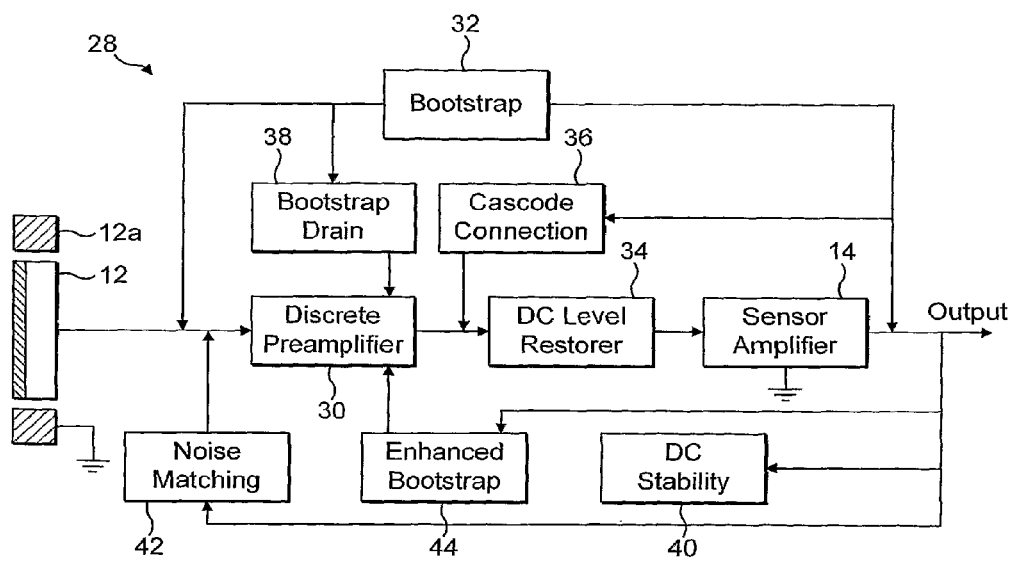
FIG. 2 is a block diagram of an electrodynamic sensor according to the present invention.

FIG. 2 is a block diagram of the sensor 28 according to the invention illustrating how these different techniques may be applied to the sensor to enhance significantly the signal to noise ratio. One embodiment of the discrete pre-amplifier stage 30, which is in practice inserted between the detection electrode 12 and the sensor amplifier 14, is shown in detail in, and further described in relation to, FIGS. 3 and 4. This embodiment includes a bootstrapping circuit 32 shown separately in FIG. 2. Another embodiment of discrete pre-amplifier stage 30, also employing the bootstrapping circuit 32 as well as a DC level restorer circuit 34, is illustrated in FIG. 5.

Figure 5:
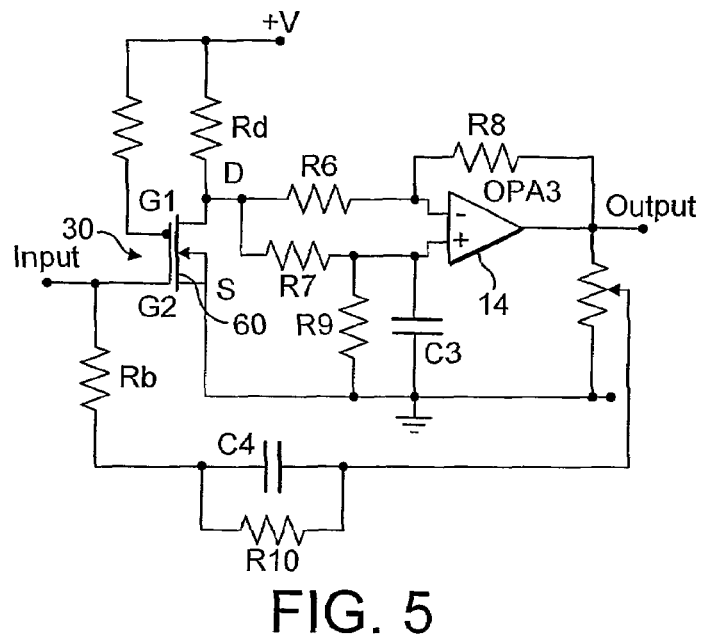
FIG. 5 is a circuit diagram of a further embodiment of discrete pre-amplifier stage provided by a FET, with bootstrapping and a DC level restorer circuit.
Figure 6:
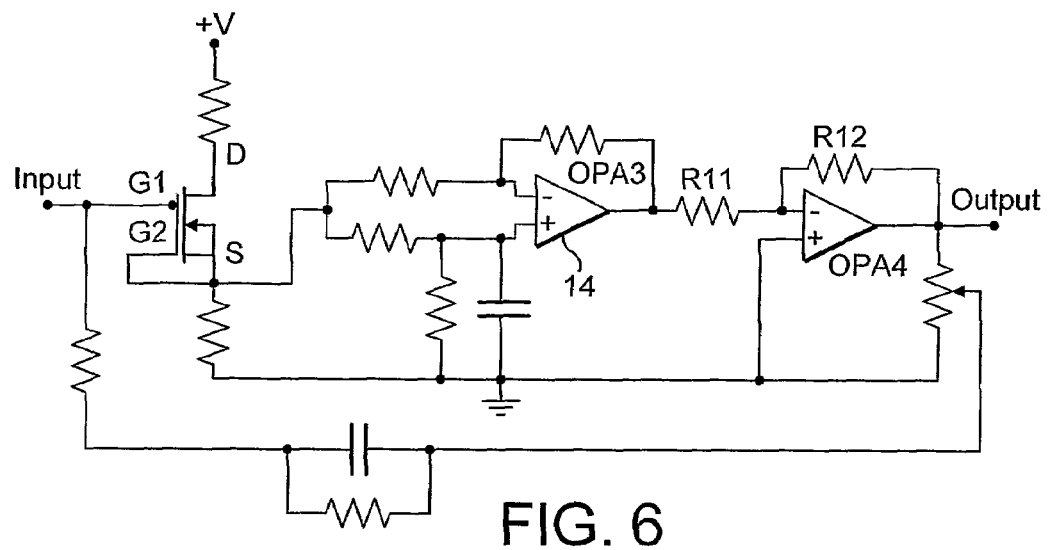
FIG. 6 is a circuit diagram of a modification of the FIG. 5 circuit having a cascode circuit for bootstrapping the source of the FET.
Figure 7:
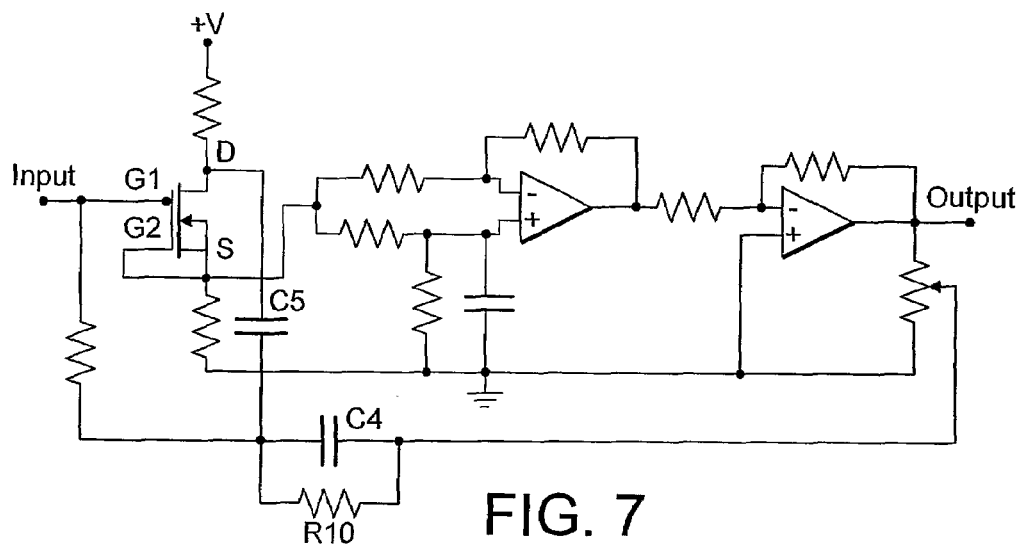
FIG. 7 is a circuit diagram of a further modification of the FIG. 5 circuit having a drain bootstrapping circuit for bootstrapping the drain of the FET.

The discrete pre-amplifier stage 30 of FIG. 5 may be further enhanced by means of additional bootstrapping, for example provided by a cascode circuit connection 36 as shown in FIG. 6 to bootstrap the source of a FET employed as the pre-amplifier stage 30, and/or provided by a drain bootstrap circuit 38 as shown in FIG. 7 to bootstrap the drain of the FET.

Further techniques for noise reduction, illustrated in FIGS. 8 to 12, may also be applied to the sensor 28. Such techniques may include the provision of a dc stability gain setting circuit 40 shown in FIG. 8 for overcoming the problem of, low frequency instability, and/or of a noise matching circuit 42 shown in FIGS. 9 and 10 for addressing the problem of low frequency noise, and/or of an enhanced bootstrap circuit 44 shown in FIGS. 11 and 12 for addressing the problem of drift reduction. These additional circuits are all applicable generally to operational amplifier based sensors, as well as particularly to the versions of the sensor 28 including a discrete pre-amplifier stage 30 as described in relation to FIG. 2. In the case of weak coupling between the detection electrode 12 and a sample under test, however, the maximum signal to noise ratio will be obtained by utilising both a discrete pre-amplifier stage 30, as described below with reference to FIGS. 2 to 7, and at least one of the techniques as described below in relation to FIGS. 8 to 12.

Discrete Pre-Amplifier Stage

For situations where the coupling capacitance $C_c$ between a sample under test and the sensor 28 is much less than the input capacitance $C_{in}$ of the sensor 28, the available measurement signal is attenuated by a capacitive potential divider made up of the capacitances $C_c$ and $C_{in}$. This is the case in practice for many remote monitoring applications and for microscopic probes, particularly for example in the field of biometric sensing. In this situation, the best way of increasing the signal to noise ratio would be to reduce the input capacitance $C_{in}$ to be less than or comparable with the coupling capacitance $C_c$. However, commercially available operational amplifiers typically have input capacitances $C_{in}$ ranging from 1-10 pF, and these cannot be reduced further. The present invention is based on the realisation that a discrete pre-amplifier stage 30 having an input capacitance as low as 0.1 pF may be employed in conjunction with the detection electrode 12 and sensor amplifier 14 effectively to achieve a lower input capacitance. The use of such a device as a front end pre-amplifier will increase the available signal by a large factor (×10-×100).

Figure 3:
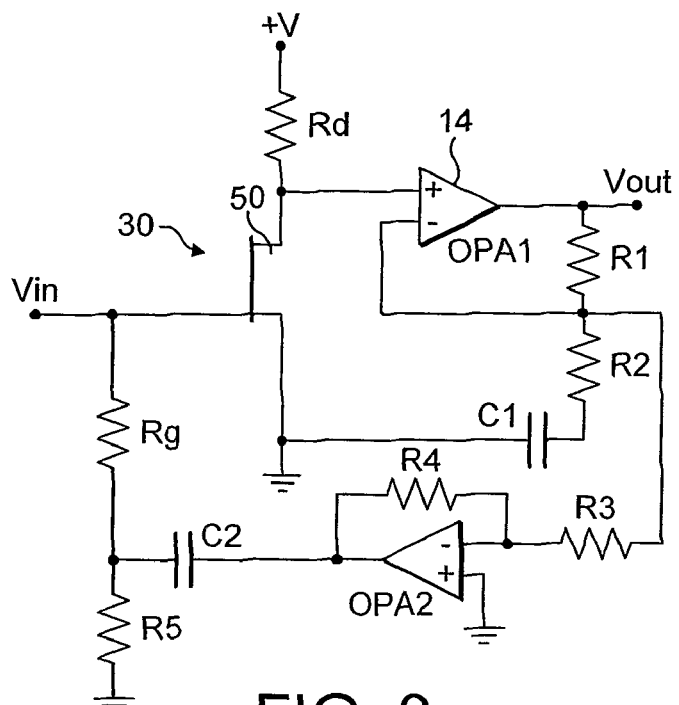
FIG. 3 is a circuit diagram of a first embodiment of a discrete pre-amplifier stage employed in the sensor of FIG. 2, with bootstrapping.

In one embodiment of the sensor 28 as shown in FIG. 3, the pre-amplifier stage 30 is achieved using a high electron mobility transistor (HEMT) device 50 situated between the detection electrode 12 of the known sensor, represented in FIG. 3 by an input $V_{in}$, and the operational amplifier 14 of the known sensor. The HEMT device 50 displays very low noise characteristics due to the extremely high mobility of the charge carriers in the semiconducting channel of the device. The HEMT device 50 is configured in this instance as a common source amplifier, with the property of inverting voltage gain. A resistor Rd limits the current flowing through the channel of the HEMT device 50, and the DC operating point is set by the voltage applied to a gate resistor Rg connected to the gate of the HEMT device 50. The output signal, taken from the drain of the HEMT device 50, is amplified by an operational amplifier OPA1, constituting the sensor amplifier 14, with the gain of the operational amplifier OPA1 set by a feedback connection of two resistors R1, R2 and a capacitor C1.

An attenuated version of the output from the operational amplifier OPA1 is fed back and amplified by way of a positive feedback loop including the bootstrap circuit 32 (see FIG. 2) comprising a further operational amplifier OPA2 arranged to provide a bootstrap signal via a capacitor C2 for the gate resistor Rg, thereby increasing the input impedance of the sensor 28. The gain of the operational amplifier OPA2 is set by two resistors R3 and R4. In addition, a resistor R5 provides a DC path for the input bias current required by the HEMT device 50.

Figure 4:
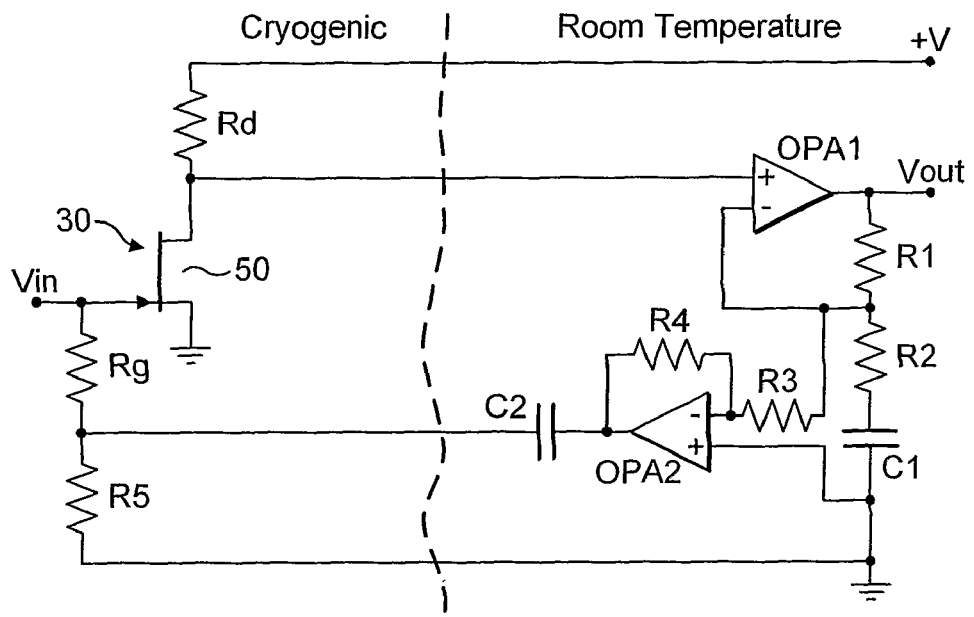
FIG. 4 is a circuit diagram of a modification of the FIG. 3 circuit.

Further enhancement of the signal to noise ratio may also be achieved by physically separating the first stage transistor 50, providing the pre-amplifier stage 30, from the following electronics and operating at a reduced temperature, for example as shown in FIG. 4. The circuit of FIG. 4 is similar to that of FIG. 3, with the exception that the portion of the circuit to the left of the dashed line is maintained at cryogenic temperatures for reduced temperature operation and the portion to the right is at room temperature.

It is to be noted that the HEMT device 50 may take the form either of a pre-amplifier in front of the sensor amplifier 14, as shown in FIGS. 3 and 4, or else may be incorporated within the feedback loop of the following amplifier OPA1. Further, the HEMT device 50 may comprise two or more devices if used differentially.

In another embodiment shown in FIG. 5, a silicon dual gate MOSFET 60 (or two FETs so connected) is employed as the pre-amplifier stage 30. The MOSFET 60 is biased by means of an appropriate drain resistor $R_d$ to give an inverting voltage gain. The input signal from the sensor electrode 12 is coupled to gate G2 of the MOSFET 60, with gate G1 of the MOSFET 60 being held at an appropriate bias voltage by means of a further resistor $R_{G1}$. An input bias current in this example is provided by a high value resistor $R_b$, typically having a resistance in the range 10-100 GΩ, to which is connected the bootstrap circuit 32, here comprising a parallel connection of a capacitor C4 and resistor R10 providing the necessary coupling and DC bias to the resistor $R_b$.

The output of the MOSFET 60 in this embodiment, taken from the drain D, contains both the amplified input signal and an unwanted DC offset. This DC offset may be removed by means of the DC level restoring circuit 34 in conjunction with the following operational amplifier circuit OPA3, which is configured as a differential amplifier and which represents the sensor amplifier 14 of the sensor 28. For this purpose, the gain of the operational amplifier OPA3 is set by resistors R6 and R8 for its inverting input and by resistors R7 and R9 for its non-inverting input. In addition, a capacitor C3 is connected across the resistor R9, so as to act as a low pass filter which rejects the AC component of the signal coupled to it, thereby leaving the DC offset. Hence, the difference signal, which is amplified by the operational amplifier OPA3, consists only of the wanted signal. This technique has the advantage that it responds to any DC drift present in the output of the MOSFET 60 and removes this from the signal below a corner frequency set by the time constant of the filter components.

The output from the operational amplifier OPA3 is suitable to provide a positive feedback signal for the guard circuit as shown in FIG. 1 and the bootstrap circuit 32 as already described, as well as a neutralisation circuit as described in International Patent Application No. WO 03/048789. An input capacitance<1 pF for the sensor 28 with the configuration of FIG. 5 has been measured in experimental trials using this embodiment.

It should be noted that the DC input bias current described above as being provided by the resistor $R_b$ may in practice be provided by one or a combination of three means: First, by leakage through the bootstrap capacitor C4 (usually the effective resistance of the capacitor is much lower than the resistance of the bias resistor); second, by the addition of the resistor R10 in parallel with the bootstrap capacitor C4; and third, by including a resistor to ground from the junction of the bias resistor $R_b$ and the bootstrap capacitor C4.

The embodiments shown in FIGS. 6 and 7 are variants of the circuit shown in and described with reference to FIG. 5, and these will now be described. Like parts are designated by the same reference signs, and will not be described further in detail.

In the version of the FIG. 5 embodiment shown in FIG. 6, the silicon dual gate MOSFET 60 is connected in a cascode configuration where the device is internally bootstrapped to the source S so that internal bootstrapping is provided within the pre-amplifier stage. Such cascode connection 36 (see FIG. 2) has the effect of greatly reducing the input capacitance $C_{in}$ both of the MOSFET 60 and, since the MOSFET 60 is the input stage of the sensor 28, of the overall sensor. For this circuit, the voltage gain of the first discrete pre-amplifier stage provided by the MOSFET 60 is unity and non-inverting. The output of the MOSFET 60 is again fed through the DC level restorer circuit 34 including the operational amplifier OPA3 (amplifier 14) and is then coupled to an inverting amplifier OPA4 to provide the correct phase of feedback signal for the bootstrap circuit 32. The gain of the operational amplifier OPA4 is set by two resistors R11 and R12. A fraction of the output from the operational amplifier OPA4 is used for the bootstrap circuit 32 as before. An input capacitance<0.2 pF has been measured in experimental trials using this configuration for the sensor 28.

A further enhancement of the FIG. 6 embodiment with the cascode circuit connection 36 is possible as shown in the embodiment of FIG. 7. According to this embodiment, an additional bootstrap 38 to the drain D of the MOSFET 60 as well as the bootstrap to the source S enables the intrinsic input capacitance to be further reduced. This additional bootstrap 38 is achieved in this instance using a bootstrap capacitor C5 connected between the MOSFET end of the parallel connection of the capacitor C4 and resistor R10 and the drain D of the MOSFET 60. It is alternatively possible to employ an independently derived bootstrap signal obtained e.g. from the other end of the parallel connection of C4/R10.

By way of example, the input capacitance may be reduced to <0.1 pF using the circuit of FIG. 7. This implies that so long as there is a coupling capacitance of ~0.1 pF or greater, an optimum signal to noise ratio would be obtained. However, for this configuration of circuit, it is anticipated that the signal would remain measurable, with a 10:1 signal to noise ratio, for coupling capacitances down to ~$10^{-15}$ F, assuming a 1 volt signal at the source.

The circuits of FIGS. 3 to 7 significantly enhance the overall response of the electric potential sensor 28 to the sample under test in situations where weak coupling occurs to the sample. However, in certain circumstances, indicated below, problems still may arise at low frequencies of operation. The circuits shown in and described with reference to FIGS. 8 to 12 address these problems.

DC Stability Gain Setting Circuit

The optimum noise performance of most amplifiers is achieved when the closed loop gain is considerably greater than unity, typically ×30–×100. Incorporating large voltage gain within the electric potential sensor 28 produces improvements in the noise performance, but may also introduce low frequency instability and increase the settling time of the sensor. One approach to alleviating this problem employs a low frequency negative feedback stabilisation loop as described in International Patent Application No. WO 03/048789. Another simple and effective technique is to introduce AC coupling into the gain setting network by employing a DC stability gain setting circuit 40 (see FIG. 2) as shown in detail FIG. 8. Such DC stability gain setting circuit 40 may advantageously be employed in combination with one or more of the techniques described with reference to the embodiments of FIGS. 3 to 7 but it may also offer benefits when employed alone in its own right.

Figure 8:
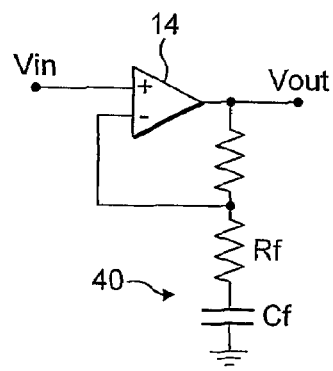
FIG. 8 is a circuit diagram of a DC stability gain setting circuit shown in FIG. 2.

More especially, the DC stability gain setting circuit 40 of FIG. 8 comprises a series connection of a resistor $R_f$ and a capacitor $C_f$ between a negative feedback loop at the output of the sensor amplifier 14 of the sensor 28 and ground, for setting the time constant for lower frequencies of operation of the sensor 28, where the time constant is given by:

$$f_c = 1/2\pi R_f C_f$$

The effect of this is to reduce the gain of the sensor amplifier 14 to unity at DC whilst maintaining a high gain at the signal frequencies, hence stabilising the sensor and improving the settling time. Hence, it is possible to achieve low noise performance with high voltage gain and stability.

Noise Matching Circuit

The noise performance of a differential input amplifier, such as the sensor amplifier 14 of the sensor 28, depends on many factors. Amongst the parameters to be considered are the level of the source impedance, ie the coupling impedance between the sample under test and the input of the sensor amplifier 14 as provided by a combination of coupling resistance $R_c$ and coupling capacitance $C_c$, compared to the input impedance, provided by a combination of input resistance $R_{in}$ and input capacitance $C_{in}$ for the amplifier 14, and the extent to which the relative contributions of the voltage and current noise combine to create overall frequency dependent noise as observed at the output of the amplifier 14. For a situation in which the coupling impedance between the sample and the input is very high (i.e. $R_c >> R_{in}$ and/or $C_c << C_{in}$), this factor may have a very large effect on the frequency dependent noise.

Figure 9:
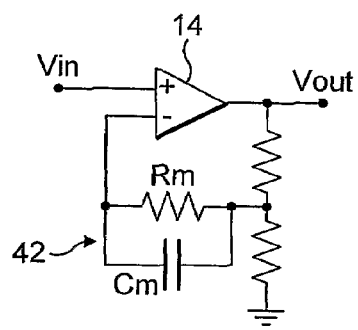
FIG. 9 is a circuit diagram of a noise matching circuit shown in FIG. 2.

Close impedance matching between the inverting and non-inverting inputs of the sensor amplifier 14 serves not only to maximise the common mode rejection ratio, but also to minimise the noise. This may be achieved by the inclusion of a frequency dependent matching network, for example as shown in FIG. 9, providing the noise matching circuit 42 of FIG. 2. In this network, a parallel combination consisting of a resistor $R_m$ and a capacitor $C_m$, where $R_m = R_c$ and $C_m = C_c$, is added to the input of the sensor amplifier 14 to achieve this balance condition and hence a reduction in the frequency dependent noise observed at the output of the sensor amplifier 14.

Figure 10:
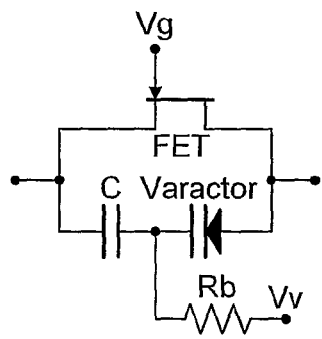
FIG. 10 is a circuit diagram of a modification of the noise matching circuit of FIG. 9.

In a variation of the FIG. 9 circuit, the parallel components $R_m$, $C_m$ could be replaced by a parallel combination of a FET and a varactor diode, with suitable biasing components, as shown in FIG. 10, to allow remotely tunable values for the resistance and capacitance for signal to noise optimisation. Bias voltages $V_g$ and $V_v$ control the resistance of the FET channel and the capacitance of the varactor diode respectively.

As in the case of the FIG. 8 circuit, the noise matching circuit 42 of FIG. 9 or 10 may advantageously be employed in combination with one or more of the techniques described with reference to the embodiments of FIGS. 3 to 7 but it may also offer benefits when employed alone in its own right.

Bootstrap with Gain

Figure 11:
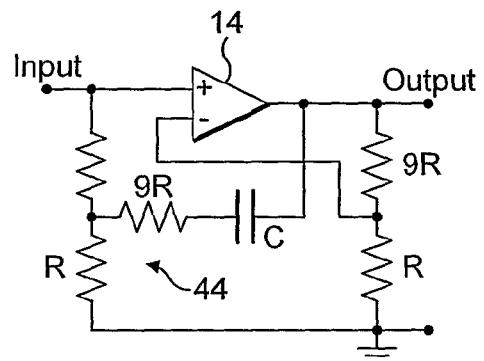
FIG. 11 is a circuit diagram of an enhanced bootstrapping circuit shown in FIG. 2.

The use of a positive feedback loop with a high pass characteristic to bootstrap the input bias network as described in International Patent Application No. WO 03/048789 significantly enhances the performance of the basic sensor 10 by increasing the input impedance. However, this technique may become difficult to implement at very low frequencies (say <1 Hz) due to the long time constant required, as set by the values chosen for the resistor R and capacitor C of the bootstrap circuit. In other words, the signal to noise ratio is reduced at low frequency. One way of addressing this problem comprises the use of an enhanced bootstrap circuit 44 as shown in FIGS. 2 and 11, which utilises a higher gain output (e.g. ×10) available from the sensor amplifier 14. For example, the provision of two gain setting resistors 9R and R at the output of the amplifier 14, signifying a 9:1 ratio for their resistance values, gives a gain of ×10. The bootstrap signal must then be precisely ×1 if maximum bootstrap and stable operation is to be achieved. In this enhanced bootstrap circuit 44, the output signal from the amplifier 14 is fed back through the bootstrap capacitor C to a 1/10 resistive attenuator, comprising further resistors R and 9R in a 9:1 ratio, shown on the left hand side of the capacitor C in FIG. 11, to provide the ×1 bootstrap signal. This results in a ×10 (for this example) increase in the time constant, therefore leading to smaller values for the capacitor C for a given lower operating frequency, or lower frequency operation.

Figure 12:
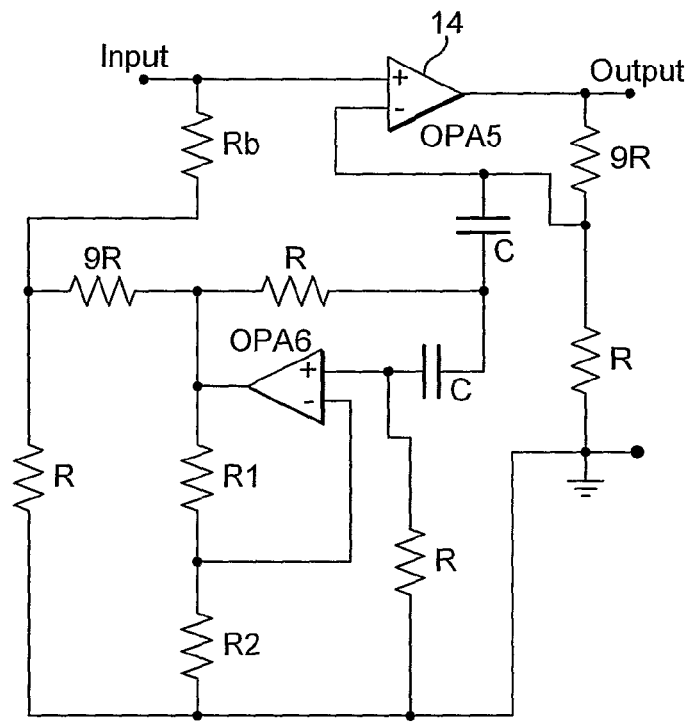
FIG. 12 is a circuit diagram of a modification of the enhanced bootstrapping circuit of FIG. 11.

A variation on the enhanced bootstrap circuit 44 of FIG. 11 uses a high pass filter to set the lower operating frequency of the bootstrap circuit as shown in FIG. 12. Here, the time constant is set by two resistor-capacitor pairs (RC) connected in the feedback circuit from the output of the amplifier 14, which RC pairs, together with a high impedance buffer amplifier OPA6, form a second order high pass filter. The gain is provided by two gain setting resistors R1 and R2.

It will be appreciated that the variation of FIG. 12 may employ either a passive high pass filter followed by a high impedance buffer amplifier or an active high pass filter, both of which enable low frequency operation to be achieved with convenient values of R and C.

Again, the enhanced bootstrap circuit 44 may advantageously be employed in combination with one or more of the techniques described with reference to the embodiments of FIGS. 3 to 7 but it may also offer benefits when employed alone in its own right.

It should also be appreciated that the circuits described with reference to FIGS. 8 to 12 may be employed individually or in combination with the techniques described with reference to the embodiments of FIGS. 3 to 7.

What is claimed is:

1. An electric potential sensor comprising:
   at least one detection electrode arranged for capacitive coupling with a sample under test and for generating a measurement signal;
   a sensor amplifier adapted to receive the measurement signal as input and to supply an amplified detection signal as output;
   input impedance enhancing means comprising at least one of a guard circuit, a bootstrapping circuit and a neutralisation circuit, said input impedance enhancing means providing a high input impedance to the sensor amplifier for increasing the sensitivity of the electrode to reduced electric potentials;
   a discrete pre-amplifier stage for increasing the amplitude of the measurement signal input to the sensor amplifier, the discrete pre-amplifier stage comprising a further amplifier arranged to co-operate with the sensor amplifier so as to reduce an input capacitance of the sensor amplifier, whereby to enhance signal measurement in instances where capacitive coupling between the sample under test and the detection electrode is equal to or less than the input capacitance of the sensor amplifier; and
   means for reducing noise amplitude in order to increase signal to noise ratio, the means for reducing noise amplitude comprising at least one of a DC stability gain setting circuit comprising means for introducing AC coupling into a network for setting the gain of the sensor amplifier, a noise matching circuit comprising means for balancing the impedance at inverting and non-inverting inputs of the sensor amplifier, and an enhanced bootstrapping circuit comprising a bootstrapping circuit including gain setting means providing feedback from the output of the sensor amplifier to an input thereof.

2. An electric potential sensor according to claim 1 in which the detection electrode is juxtaposed with a conducting element connected to a zero reference potential, whereby to reduce the effective distance from the detection electrode to an earthing point and thereby reduce effective source impedance.

3. An electric potential sensor according to claim 2 in which the conducting element is an annular ring surrounding the detection electrode.

4. An electric potential sensor according to claim 1 in which the input impedance enhancing means comprises a guard circuit, a bootstrapping circuit and a neutralisation circuit.

5. An electric potential sensor according to claim 1 in which the discrete pre-amplifier stage is situated between the detection electrode and the sensor amplifier.

6. An electric potential sensor according to claim 1 in which the discrete pre-amplifier stage is situated in a feedback loop of the sensor amplifier.

7. An electric potential sensor according to claim 1 in which the discrete pre-amplifier stage is physically separated from the sensor amplifier in a zone which is maintained at a different temperature from the sensor amplifier.

8. An electric potential sensor according to claim 1 in which the discrete pre-amplifier stage comprises a high electron mobility transistor.

9. An electric potential sensor according to claim 1 in which the discrete pre-amplifier stage comprises a FET arrangement.

10. An electric potential sensor according to claim 1 in which an output of the discrete pre-amplifier stage is supplied to the sensor amplifier by way of a DC level restorer circuit to remove at least one of unwanted DC drift and offset.

11. An electric potential sensor according to claim 1 in which the discrete pre-amplifier stage is internally bootstrapped.

12. An electric potential sensor according to claim 11 in which a cascode circuit connection provides the internal bootstrapping.

13. An electric potential sensor according to claim 11 in which a drain bootstrap circuit provides the internal bootstrapping.

14. An electric potential sensor comprising:
   at least one detection electrode arranged for capacitive coupling with a sample under test and for generating a measurement signal;
   a sensor amplifier adapted to receive the measurement signal as input and to supply an amplified detection signal as output;
   input impedance enhancing means comprising at least one of a guard circuit, a bootstrapping circuit and a neutralisation circuit, said input impedance enhancing means providing a high input impedance to the sensor amplifier for increasing the sensitivity of the electrode to reduced electric potentials;
   a discrete pre-amplifier stage for increasing the amplitude of the measurement signal input to the sensor amplifier, the discrete pre-amplifier stage comprising a further amplifier arranged to co-operate with the sensor amplifier so as to reduce an input capacitance of the sensor amplifier, and
   means for reducing noise amplitude comprising at least one of a DC stability gain setting circuit comprising means for introducing AC coupling into a network for setting the gain of the sensor amplifier, a noise matching circuit comprising means for balancing the impedance at inverting and non-inverting inputs of the sensor amplifier, and an enhanced bootstrapping circuit comprising a bootstrapping circuit including gain setting means providing feedback from the output of the sensor amplifier to an input thereof.

* * * * *